(12) United States Patent
Sakamoto et al.

(10) Patent No.: US 8,216,559 B2
(45) Date of Patent: Jul. 10, 2012

(54) DEODORANT FIBER AND FIBROUS ARTICLE AND PRODUCT MADE THEREOF

(75) Inventors: Kazuyuki Sakamoto, Moriyama (JP); Akinori Maekawa, Moriyama (JP)

(73) Assignee: JNC Corporation, Tokyo (JP)

( * ) Notice: Subject to any disclaimer, the term of this patent is extended or adjusted under 35 U.S.C. 154(b) by 1034 days.

(21) Appl. No.: 11/113,666

(22) Filed: Apr. 25, 2005

(65) Prior Publication Data

US 2005/0255078 A1 Nov. 17, 2005

(30) Foreign Application Priority Data

Apr. 23, 2004 (JP) ................................ 2004-128627

(51) Int. Cl.
*A61L 9/00* (2006.01)
*A61L 9/01* (2006.01)

(52) U.S. Cl. ..................................................... 424/76.1

(58) Field of Classification Search .................. None
See application file for complete search history.

(56) References Cited

U.S. PATENT DOCUMENTS

| | | | | |
|---|---|---|---|---|
| 3,891,594 A | * | 6/1975 | Taylor ........................... | 523/313 |
| 5,690,922 A | * | 11/1997 | Mouri et al. ................. | 424/76.1 |
| 5,726,001 A | * | 3/1998 | Eichorst ........................ | 430/523 |
| 5,925,455 A | * | 7/1999 | Bruzzone et al. ............. | 428/328 |
| 6,184,280 B1 | * | 2/2001 | Shibuta ......................... | 524/405 |
| 6,252,003 B1 | * | 6/2001 | Kuwahara et al. ............ | 525/242 |
| 6,652,166 B2 | * | 11/2003 | Kawasaki et al. ............. | 396/513 |
| 2003/0064651 A1 | * | 4/2003 | Nakai et al. ................... | 442/361 |
| 2003/0094600 A1 | * | 5/2003 | Dobler et al. ................. | 252/500 |

* cited by examiner

*Primary Examiner* — David J Blanchard
*Assistant Examiner* — Trevor Love
(74) *Attorney, Agent, or Firm* — Hamre, Schumann, Mueller & Larson, P.C.

(57) ABSTRACT

A deodorant fiber comprises a thermoplastic resin containing 0.1 to 10 weight %, with respect to the weight of said fiber, of a complex oxide comprising oxides of at least two metals selected from the divalent or trivalent metals, and coated with 0.1 to 5 weight %, with respect to the weight of said fiber, of an agent comprising a surfactant composition comprising 20-80 weight % of the component A and 80-20 weight % of the component B and/or the component C. The A is at least one compound selected from a group consisting of betaine amphoteric compounds, carbonyl compounds and vinyl ether-maleic anhydride copolymers. The B is a nonionic surfactant comprising at least one substance selected from a group consisting of nonionic surfactants based on alkylene oxide adducts and nonionic surfactants based on polyvalent alcohols. The component C is an anionic surfactant comprising at least one substance selected from a group consisting of carbonates, sulfonates, sulfate ester salts and phosphate ester salts.

12 Claims, No Drawings

DEODORANT FIBER AND FIBROUS ARTICLE AND PRODUCT MADE THEREOF

BACKGROUND OF THE INVENTION

The present invention relates to deodorant fibers, or more specifically, to deodorant fibers suitable as the starting materials for applications including absorptive products such as diapers and napkins, medical and hygienic materials, and materials for home products, general medical products, bedclothes, filters, nursing care goods, and items for pets.

Recent changes in lifestyles, including more closely packed residences and enhanced air-tightness of buildings, have increased needs for odor prevention and/or control. Typical odor sources include basic gases such as ammonia and trimethylamine, sulfur-containing substances such as hydrogen sulfide and methylmercaptan, and lower fatty acids such as acetic acid, lactic acid, valeric acid and caproic acid, which are formed by biodegradation of excretion from the sweat and sebaceous glands. Nitrogen-containing ring compounds such as indole and skatole also are known malodorous substances.

Several methods to remove such odorous substances are known. Typical examples include physical absorption using porous materials such as active carbon or silica gel; chemical methods in which the substances are eliminated by neutralization or oxidation reactions; and sensory methods by which the perception of odor is canceled or masked by a strong perfume. The chemical methods are particularly effective in that they eliminate odorous substances at high concentrations quickly. In fact, a variety of deodorizing agents have been developed.

However, many of the currently used chemical deodorants are effective against ammonia, amines and other nitrogen-containing compounds but not against sulfur-containing compounds, or vice versa. As a matter of fact, few single deodorants are effective against a wide range of odorous substances including lower fatty acids. A variety of improved deodorants have been suggested; examples are a bactericidal and deodorizing agent containing amphoteric surfactants with isoelectric points over 7, amphoteric surfactants with isoelectric points under 7, nonionic surfactants and silicone oil (as in Reference 1); and a liquid deodorant containing as active ingredients betaine amphoteric compounds and ketocarboxylic acids (as in Reference 2). Some complex oxides containing two or more metals also have been proposed that provide an antibacterial or deodorizing activity when a part of the metals are activated (as in Reference 3).

The deodorants mentioned in References 1 and 2 are mostly in the liquid state, and often used as a coating on fiber surface for an effective deodorizing action. Being excellent deodorants in the liquid state, however, those substances usually lose most of their activity when deposited on fiber surfaces, due to attrition by fiber-metal or fiber-fiber friction during fiber opening (e.g. formation of web or sliver in a carding or air laying machine) or by vaporization during the heat treatment for nonwoven fabric manufacture. The final products are effective against ammonia, amines and other nitrogen-containing compounds only.

The deodorants described in Reference 3 are heat-resistant and effective against a relatively wide range of malodorous substances, but, unlike deodorants based on neutralization reactions, they are slow in action and therefore hardly effective against ammonia, amines and other nitrogen-containing compounds.

Reference 1: JP2002-47105
Reference 2: JP2717209
Reference 3: JP11-209258

SUMMARY OF THE INVENTION

The present invention provides deodorant fibers that suffer little loss of the deodorizing activity during manufacturing of nonwovens and other products in the fiber opening and sheet formation steps, and effectiveness against a wide range of malodorous substances, as well as formed materials and products made thereof. A fiber of the present invention may be characterized as follows.

A deodorant fiber comprises a thermoplastic resin containing 0.1 to 10 weight %, with respect to the weight of said fiber, of a complex oxide consisting of oxides of at least two metals selected from the divalent or trivalent metals, and coated with 0.1 to 5 weight %, with respect to the weight of said fiber, of an agent containing as a main ingredient a surfactant composition comprising 20-80 weight % of the component A and 80-20 weight % of the component B and/or the component C. The component A is at least one compound(s) selected from a group consisting of betaine amphoteric compounds, carbonyl compounds and vinyl ether-maleic anhydride copolymers. The component B is a nonionic surfactant including at least one substance(s) selected from a group consisting of nonionic surfactants based on alkylene oxide adducts and nonionic surfactants based on polyvalent alcohols. The component C is an anionic surfactant including at least one substance(s) selected from a group consisting of carbonates, sulfonates, sulfate ester salts and phosphate ester salts.

In the deodorant fiber described above, the complex oxide may be represented by either the following formula (1):

$$M^{2+}_{(1-x1)}M^{3+}_{(x1-\delta)}O \tag{1}$$

wherein $M^{2+}$ is zinc or a zinc-containing divalent metal; $M^{3+}$ is a trivalent metal selected from a group consisting of Al; Fe and Ce; $x1$ is a number in a range $0 < x1 \leq 0.5$; and $\delta$ is cationic lattice defect, or the following formula (2):

$$(M_1^{2+})_{1-x2}(M_2^{2+})_{x2}O \tag{2}$$

wherein $M_1$ is Mg and/or Ca; $M_2$ is Cu and/or Zn; and $x2$ is a number in a range $0.0001 \leq x2 \leq 0.5$.

The deodorant fiber as described above may be a conjugate fiber comprising at least two thermoplastic resins, into at least one of which has been kneaded 0.1-10 weight %, with respect to the weight of said fiber, of said complex oxide, the surface of the conjugate fiber being coated with 0.1-5 weight %, with respect to the weight of said fiber, of an agent containing as a main ingredient a surfactant including 20-80 weight % of the component A and 80-20 weight % of the component B and/or the component C.

In the deodorant fiber described above, the fiber may be a sheath-core conjugate fiber, with the complex oxide being kneaded into the sheath component of the fiber.

In the deodorant fiber as described above, at least 0.1 weight %, with respect to the weight of said fiber, of the component A may be deposited onto said fiber.

A fibrous article of the present invention comprises a deodorant fiber as described above. A fiber product of the present invention comprises either a deodorant fiber as described above or the fibrous article described above.

The deodorant fiber according to this invention includes a thermoplastic resin containing a complex oxide of at least two metals selected from the bivalent or trivalent metals, on which an agent including the component A and the component B and/or C is deposited. The deodorizing agent is also antibacterial, antistatic and heat-resistant, and is not easily separated from fiber surface. A particular advantage of the fiber is the effectiveness against all of the three principal classes of malodorous substances, i.e. bases such as ammonia and amines, acids such as acetic acid, and sulfur-containing compounds such as hydrogen sulfides. The fiber also has a high absorption rate.

DETAILED DESCRIPTION OF THE INVENTION

The invention now is described below in further detail. The invention is not considered to be limited to the specific details.

The deodorant fiber according to the invention includes a thermoplastic resin containing a complex oxide of at least two metals selected from the bivalent or trivalent metals, on which 0.1-5 weight %, with respect to the weight of said fiber, of an agent including 20-80 weight % of the component A and 80-20 weight % of the component B and/or C is deposited.

The complex oxides used in the invention may characterized by including a principal ingredient represented by either the following formula (1):

$$M^{2+}_{(1-x1)}M^{3+}_{(x1-\delta)}O \quad (1),$$

wherein $M^{2+}$ is zinc or a zinc-containing divalent metal, $M^{3+}$ is a trivalent metal selected from a group consisting of Al, Fe and Ce, $x_1$ is a number in a range $0 < x_1 \leq 0.5$, and $\delta$ is cationic lattice defect,
or the following formula (2):

$$(M_1^{2+})_{1-x2}(M_2^{2+})_{x2}O \quad (2),$$

wherein $M_1$ is Mg and/or Ca, $M_2$ is Cu and/or Zn, and $x_2$ is a number in a range $0.0001 \leq x_2 \leq 0.5$. Oxides of both (1) and (2) may be included if desired, and more than one oxide of each formula may be included. The "principal ingredient" means that the complex oxides of formula (1) and/or (2) account for at least 50% by mass of oxide added to the fiber, preferably at least 80%.

The zinc oxide-based complex oxide of the formula (1) is a solid solution based on ZnO wherein $M^{3+}$ (e.g. Al) is substituted for Zn, having the same crystal structure as that of ZnO, or a mixture of said solid solution with a spinel ($M^{2+}M^{3+}_2O_4$). The complex oxide gives a powder x-ray diffraction pattern similar to that of ZnO. The complex oxide of the formula (2) is a solid solution based on magnesium oxide and/or calcium oxide containing $Cu^{2+}$ and/or $Zn^{2+}$ having the same crystal structure as that of MgO or CaO. This oxide gives a powder x-ray diffraction pattern similar to that of MgO or CaO.

The complex oxide of the formula (1) may contain $Al_2O_3$, $Fe_2O_3$ or $Ce_2O_3$ as long as the characteristics of the solid solution, and thus the deodorizing activity, remain unaffected. On the other hand, the $M^{3+}$ content should not be zero, since the deodorizing activity depends on the activation of $M^{2+}$. Therefore the value of $x_1$ should preferably not exceed 0.5 to keep the concentration of $Al_2O_3$, $Fe_2O_3$ or $Ce_2O_3$ sufficiently low. The preferred range for x1 can thus be set as $0 < x_1 \leq 0.5$; a more desirable range is $0.1 \leq x_1 \leq 0.4$, or still more desirably $0.2 \leq x_1 \leq 0.4$. $M^{2+}$ may be Zn or a Zn with bivalent metal(s). Specifically, Ca, Mg or Cu as the bivalent metal(s) gives a substance with sufficient performance and safety.

The complex oxide of the formula (2) may contain CuO and/or ZnO as long as the characteristics of the solid solution, and thus the deodorizing activity, remain unaffected. On the other hand, Cu and/or Zn, are useful for the deodorizing and antibacterial activity, and are desirable, even in a small amount, for activation of magnesium and/or calcium to provide satisfactory performance of the product. A value of $x_2$ of 0.5 or less effectively compensates possible existence of CuO and/or ZnO in the complex oxide of the formula (2), and one of 0.0001 or more is enough for acceptable deodorizing activity and activation of the magnesium and/or calcium. A preferred range for x2 can thus be set as $0.0001 \leq x_2 \leq 0.5$; a more desirable range is $0.0005 \leq x_2 \leq 0.4$, or still more desirably $0.001 \leq x_1 \leq 0.2$.

The concentration of the complex oxide used in the present invention, as well as the concentration ratio of bivalent or trivalent metals ($M^{2+}/M^{3+}$ for the formula (1), $M_1^{2+}/M_2^{2+}$ for the formula (2)), may be determined by the fluorescent x-ray analysis or x-ray photoelectron spectroscopy of the complex oxide particles on the fiber surface, or the elemental analysis of the complex oxide isolated by filtration or centrifugation of a solution of the thermoplastic resin constituting the fiber in an appropriate solvent, using the surface analysis as described above, atomic absorption analysis or IPC spectroscopy. While other analytical methods are available for this purpose, the techniques mentioned above are preferably combined in that they become easier to distinguish between a solid solution of bivalent and/or trivalent metal oxides and mixtures of different metal oxides.

The preferable concentration of the complex oxide of the formula (1) or (2) used in the invention is 0.1-10 weight % with respect to the fiber weight. The concentration of 0.3 to 5 weight % is more preferable, still more preferably 0.5 to 5 weight %. A concentration of 0.1 weight % or higher assures sufficient deodorizing activity, while a concentration of 10 weight % or lower reduces impairment of the spinning characteristics and separation of said oxide from the fiber during the nonwovens manufacturing process, thus ensuring satisfactory productivity.

The component A used in the deodorant fiber of the invention includes at least one compound(s) selected from a group consisting of betaine amphoteric compounds, carbonyl compounds and vinyl ether-maleic anhydride copolymers; the component B includes at least one nonionic surfactant selected from a group consisting of nonionic surfactants based on alkylene oxide adducts and polyvalent alcohol-based nonionic surfactants; and the component C includes at least one anionic surfactant selected from a group consisting of carbonates, sulfonates, sulfate ester salts and phosphate ester salts. The reference herein to "at least one selected from a group consisting of . . . and . . . " includes one or more species from one or more of any generic elements listed, and does not require one from of each generic element unless clearly indicated by the context.

One of the betaine amphoteric compounds conveniently used in the invention as the component A is an amidobetaine represented by the formula (3):

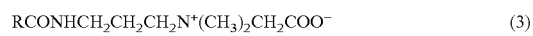
$$RCONHCH_2CH_2CH_2N^+(CH_3)_2CH_2COO^- \quad (3)$$

where R is an alkyl group with 1-20 carbon atoms.

One of the other betaine amphoteric compounds conveniently used in the invention is imidazolium compounds represented by the formula (4):

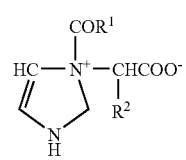

(4)

where $R^1$ is an alkyl group with 1-7 carbon atoms and $R^2$ is an alkyl group with 8 or more carbon atoms.

Examples of the amidobetaines include: octyldimethylaminoacetic acid betaine, 2-ethylhexyldimethylaminoacetic acid betaine, decyidimethylaminoacetic acid betaine, 2-methylnonyldimethylaminoacetic acid betaine, lauryldimethylaminoacetic acid betaine, palm oil alkyl dimethylaminoacetic acid betaine, myristyldimethylaminoacetic acid betaine, palmityidimethylaminoacetic acid betaine, stearyidimethylaminoacetic acid betaine, lauryidihydroxymethylaminoacetic acid betaine, palm oil alkyl dihydroxymethylaminoacetic acid betaine, octanamide propyldimethylaminoacetic acid betaine, 2-ethylhexanamide propyldimethylaminoacetic acid betaine, decanamide propyldimethylaminoacetic acid betaine, 2-methylnonanamide propyldemethylaminoacetic acid betaine, laurynamide propyldimethylaminoacetic acid betaine, palm oil fatty acid amide propyldimethylaminoacetic acid betaine, myristinamide propyldimethylaminoacetic acid betaine, palmitinamide propyldimethylaminoacetic acid betaine, stearinamide propyldimethylaminoacetic acid betaine, and palm oil fatty acid amide propyldihydroxymethylaminoacetic acid betaine, as well as their mixtures.

Examples of the imidazolium amphoteric compounds include: 2-($C_6$-$C_{22}$)alkyl-N-carboxy($C_1$-$C_3$)alkyl-N-hydroxy($C_1$-$C_3$)imidazol ium betaines (e.g. 2-decyl-N-carboxymethyl-N-hydroxymethylimidazolium betaine, 2-lauryl-N-carboxymethyl-N-hydroxymethylimidazolium betaine, 2-myristyl-N-carboxymethyl-N-hydroxymethylimidazolium betaine, 2-palm oil alkyl-N-carboxymethyl-N-hydroxymethylimidazolium betaine, 2-palmityl-N-carboxymethyl-N-hydroxymethylimidazolium betaine) and 2-(C8-C18)alkyl-N-carboxymethyl-N-hydroxyethylimidazolium betaines (e.g. 2-decyl-N-carboxymethyl-N-hydroxyethylimidazolium betaine, 2-lauryl-N-carboxymethyl-N-hydroxyethylimidazolium betaine, 2-myristyl-N-carboxymethyl-N-hydroxyethylimidazolium betaine, 2-palm oil alkyl-N-carboxymethyl-N-hydroxyethylimidazolium betaine, 2-palmityl-N-carboxymethyl-N-hydroxyethylimidazolium betaine) as well as their mixtures.

Examples of the carbonyl compounds used in the invention as the component A include: monovalent aldehydes such as crotonaldehyde, allyl aldehyde, cinnamic aldehyde, octyl aldehyde, nonyl aldehyde and citronellal; bivalent aldehydes such as glyoxal; aromatic aldehydes such as benzaldehyde; aldehydic alcohols such as glycol aldehydes; aldehydic carboxylic acids such as glyoxylic acid, lactaldehyde, and glucuronic acid; aliphatic saturated ketones such as acetone, methyl ethyl ketone, dibutyl ketone, ionones, and acetylacetone; aromatic ketones such as benzophenone; ketoaldehydes such as methylglyoxalic acid; ketoalcohols such as acetol and dimethylketol; and ketocarboxylic acids such as pyruvic acid, benzoylformic acid, phenylpyruvic acid, acetoacetic acid, propionylacetic acid, benzoylacetic acid, levulinic acid, and β-benzoylpropionic acid.

Examples of the vinyl ether-maleic anhydride copolymers used in the invention as the component A include: ethylene-maleic anhydride copolymer; alkyl vinyl ether-maleic anhydride copolymers such as methyl vinyl ether-maleic anhydride copolymer or ethyl vinyl ether—maleic anhydride copolymer; and styrene-maleic anhydride copolymer, as well as their mixtures. Alkyl vinyl ether-maleic anhydride copolymers are preferable choices; methyl vinyl ether-maleic anhydride copolymer is still more desirable.

The component A may be a mixture of two ore more of the compounds listed above. In addition, oxyfatty acids, organic acids, or alkali halogenates may be added to the component A to enhance deodorizing activity.

Examples of said oxyfatty acids include: lower oxyfatty acids such as glycolic acid, lactic acid, hydroacrylic acid, α-oxylactic acid, glyceric acid, malic acid, tartaric acid or citric acid; unsaturated oxyfatty acids such as propenylglycolic acid, parasorbic acid, ricinolic acid, or 16-oxy-7-hexadecenoic acid; saturated monooxy fatty acids (containing one hydroxyl group) such as 2-oxypalmitic acid or oxystearic acid; and polyoxy fatty acids (containing two or more hydroxyl groups) such as dioxysteraric acid or trioxypalmitic acid.

Examples of said organic acids include: pyrolignous acid or its component lower fatty acids; middle fatty acids, lauric acid, oleic acid, palmitic acid, glyoxylic acid, and humic acid. Humic acids for this application should preferably have as high a base exchange capacity as possible.

Alkali halogenates have a general formula $MXO_3$, where M is an alkali metal and X is a halogen. The present invention preferably uses compounds of this formula wherein M is sodium or potassium and X is chlorine, bromine or iodine. The most suitable combination is potassium bromate.

While the component A described above is an effective and fast acting deodorant against nitrogen-containing malodorous substances, the component simply deposited on the fiber may fall off by the friction of the fiber with the carding or air-laying machine during the process of web or sliver formation. The friction also gives rise to an electrostatic charge, rendering the fiber processing difficult. These problems may be overcome by the component B and/or component C mixed with, or coated over, the component A, which obviates electrostatic charge even in a high-speed carding machine, and prevents separation of the component A from the fiber. The component B and/or component C also enhance the deodorizing performance of the system.

The component B used in the invention may be a nonionic surfactant based on alkylene oxide adducts (component B1) or a nonionic surfactant based on polyvalent alcohols (component B2).

The alkyl group in the nonionic surfactants used as the component B may contain 12 to 24 carbon atoms, any —$CH_2$— in which may optionally be replaced by —CH=CH—, cycloalkylene, or cycloalkenylene. The alkyl may be derived from natural fats or oils such as palm oil, beef fat, rapeseed oil, rice bran oil or fish oil, or from synthetic substances.

The component B1 is obtained by direct addition of an alkylene oxide to a higher alcohol, higher fatty acid or alkylamine; reaction of a higher fatty acid with a polyethylene glycol formed by addition of an alkylene oxide to a glycol; or addition of an alkylene oxide to an ester formed in a reaction of a polyvalent alcohol with a higher fatty acid.

The alkylene oxide used in the component B1 may be ethylene oxide, propylene oxide, butylene oxide or random or block adducts of ethylene oxide and propylene oxide, preferable choices including ethylene oxide and a random or block adduct of ethylene oxide with propylene oxide. Addition of 5 to 50 moles of the alkylene oxide is preferable, 50-100 weight % whereof should preferably be ethylene oxide. Hereinafter EO (n) means n moles of ethylene oxide added.

Examples of the component B1 include: polyoxyalkylene alkyl ethers (component B1-1), polyoxyalkylene esters of higher fatty acids (component B1-2), polyoxyalkylene polyvalent alcohol esters of higher fatty acids (component B1-3), polyoxyalkylene alkylphenyl ethers (component B1-4), polyoxyalkylene alkylamino ethers (component B1-5), and polyoxyalkylene alkylalkanol amides (component B-6).

The higher fatty acids used in the components B1-2, B1-3, B1-6 and B2 may generally be derived from natural products such as palm oil, beef fat, rapeseed oil, rice bran oil or fish oil; synthetic higher fatty acids may also be used.

The polyvalent alcohols used in the components B1-3 and B2 may be tri- to octavalent alcohols such as glycerin, trimethylolpropane, pentaerythritol, sorbitan, sorbitol, or sucrose. Particularly preferable choices include glycerin, pentaerythritol, sorbitan and sorbitol.

The alkylphenyl groups contained in the component B1-4 may be monoalkylphenyl or dialkylphenyl groups with 8-12 carbon atoms.

The alkylamino groups contained in the component B1-5 may be monoalkylamino or dialkylamino groups with 8-24 carbon atoms; any —$CH_2$— in the alkyl may optionally be replaced by a —CH=CH—, cycloalkylene or cycloalkenylene.

The alkylalkanolamides contained in the component B1-6 is formed by dehydration reaction of alkanolamines with higher fatty acids. The alkanolamines include monoethanolamine, diethanolamine, and monoisopropanolamine.

Nonionic surfactants based on polyvalent alcohols, such as the components B1-1 to B1-3, B1-6, glycerin, pentaerythritol, sorbitan and sorbitol, are particularly preferable substances as the component B in the invention.

The anionic surfactant used as the component C in the invention is at least one of carbonates, sulfonates, sulfate ester salts or phosphate ester salts. Specific examples of the carbonates include soaps such as potassium oleate or sodium laurate. Examples of the sulfonates include alkylsulfonates such as sodium laurylsulfonate or sodium cetylsulfonate, and alkylbenzenesulfonates such as lauryl benzenesulfonate. Examples of the sulfate ester salts include alkyl sulfate ester salts such as sodium stearyl sulfate, and alkyl(polyoxyalkilene)sulfate ester salts such as the sodium salt of the sulfuric acid ester of the adducts of lauryl alcohol with oxyalkylenes. Examples of the phosphate ester salts include phosphate ester salts of higher alcohols such as stearyl alcohol or of their adducts with polyoxyalkylenes. Higher alcohols and polyoxyalkylene adducts with alkali metal salts of sulfates and phosphates are preferable due to their antistatic property; the alkali metal salts of phosphates are still more desirable because they smooth the fiber surface.

The higher alcohol component of the alkali metal phosphate ester should preferably have 6 to 24, or more desirably 8 to 22, carbon atoms. Examples of such alcohols include decyl alcohol, lauryl alcohol, myristyl alcohol, stearyl alcohol and behenyl alcohol. Fully neutralized salts of the esters of those alcohols are preferable as the component C. Alcohols with less than six carbon atoms lead to higher friction between the fiber and metal, resulting in higher resistance in carding and, therefore, loss of the deodorant as well as winding of the fiber around the cylinder. On the other hand, alcohols with more than 24 carbon atoms tend to reduce the antistatic performance of the agent. The agent may be rendered either hydrophilic or hydrophobic by adjusting the number of carbon atoms within the range indicated above in the phosphate alkali metal salt mentioned above (see e.g. JP7-216737 and JP 10-46470). The polyoxyalkylenes used in the invention should contain oxyalkylene units with 2-4 carbon atoms such as oxyethylene, oxypropylene or oxybutylene, and the addition amount of such units is preferably 2 to 10 mole. The polyoxyalkylene may consist of either oxyethylene units only or oxyethylene units in random and/or block combination with other oxyalkylene units. Examples of the counterions in the neutral salts of phosphates include alkali metals such as K or Na, ammonia and amines, among which K and Na are preferable choices for antistatic performance.

The fiber treating agent used in the invention primarily including said surfactants contains said component A and component B and/or C in a weight ratio of 20/80 to 80/20, or desirably 25/75 to 75/25, or still more desirably 30/70 to 70/30. The portion less than 20 weight % of the component A does not provide sufficient deodorizing activity against nitrogen-containing malodorous substances, while the portion exceedingly greater than 80% tends to reduce antistatic performance of the agent and its adherence to the fiber. The amount of the agent deposited on the fiber relative to the weight of the fiber is 0.1-5%, or desirably 0.2-3%, or still more desirably 0.3-1.5%. While deposition of 0.1-5 weight % of the agent renders the fiber deodorizing and antistatic, presence of the component A of at least 0.1 weight % is desirable for sufficient deodorizing performance. The presence of components A and B and/or C as a "main ingredient" in the agent means that these components compose at least about 50% of the agent by mass.

The relative weight of the fiber treating agent deposited on the fiber may be determined by measuring the weight difference of the fiber before and after dipping in an ethanol-water (50/50) mixture for 10 minutes at 60° C., dehydrating, dipping again in the same mixture for 10 minutes at 60° C., and drying, using the formula:

Amount deposited (weight %)=[(W1−W2)/W2]*100 where W1 is the weight of the dry fiber before dipping, in g, and W2 the weight of the dry fiber after dipping, in g.

The limits of the amount deposited of the agent are provided in order to maintain the ease of the fiber opening process; they may therefore be exceeded if the fiber is formed into fibrous articles after the opening step, without impairing the advantage of the invention. The agent is applied preferably as a finishing agent in a form of solution in water to facilitate the deposition process.

While the components B and C used in the fiber treating agent according to the invention may be present singly, the use of both of the two components is preferable in that it provides a good balance of antistatic performance and fiber smoothness, thus facilitating the fiber opening process.

The fiber treating agent used in the invention may contain an amount that does not affect the advantage of the invention of a cationic antibacterial agent, for example alkyldimethylbenzyl ammonium salts such as benzalconium chloride, alkylpyridinium salts such as cetylpyridinium chloride, quaternary ammonium salts such as dialkyldimethylammonium salts, or polylysine.

Likewise, the fiber treating agent may contain a pH regulation agent such as alkanolamines containing 2-4 carbon atoms; chelating agent such as EDTA or sodium polyphosphate; skin protecting agent such as squarane or sodium hyaluronate; plant extracts such as tea leaf catechin, licoris extract or aloe extract; water repellent such as dimethylpolysiloxanes (silicone oils) or perfluoroalkyl-containing compounds; fragrances such as limonene, phenylethyl alcohol or hexylcinnamic aldehyde; preservative; antirust agent; or antifoaming agent. The amount of these additives is not included in the amount of the components A, B and C because they generally are used in very small amounts only.

The fiber used in the invention preferably includes a polyolefin, polyester or polyamide resin; fiber or nonwoven fabric including a thermoplastic elastomer based on these resins is suitable as well. The polyolefin may be high-density polyethylene, linear low-density polyethylene, low-density polyethylene, polypropylene (homopolymer), an ethylene-propylene copolymer principally including propylene, an ethylene-propylene-buten-1 copolymer principally including propylene, polybutene-1, polyhexene-1, polyoctene-1, poly(4-methylpentene-1), polymethylpentene, 1,2-polybutadiene, or 1,4-polybutadiene. In addition, the polymer may contain a small amount of an α-olefin, such as ethylene, butene-1, hexene-1, octene-1 or 4-methylpentene-1, which are not a constituent of said homopolymer, as a comonomer. A small amount of ethylene-based unsaturated monomer, such as butadiene, isoprene, 1,3-pentadiene, styrene or α-methylstyrene, may be contained as well. In addition, a mixture of two or more of said monomers may be used to form the fiber. The polyolefins may be manufactured by either the Ziegler-Natta process or a process using a metallocene-based catalyst.

A polyester resin is obtained by polycondensation of a diol and a dicarboxylic acid. Dicarboxylic acids used for this purpose may include terephthalic acid, isophthalic acid, 2,6-naphthalenedicarboxylic acid, adipic acid and sebacic acid; diols used may include ethylene glycol, diethylene glycol, 1,4-butanediol, neopentyl glycol, and 1,4-cyclohexanedimethanol. A preferred polyester for this invention is polyethylene terephthalate. The polyester may be either a homopolymer or a copolymer (copolyester) using a comonomer such as a dicarboxylic acid such as adipic acid, sebacic acid, phthalic acid, isophthalic acid or 2,6-naphthalenedicarboxylic acid, and a diol such as diethylene glycol or neopentyl glycol.

The polyamide may be nylon-4, nylon-6, nylon-46, nylon-66, nylon-610, nylon-11, nylon-12, polymetaxylenadipamide (MXD-6), polyparaxylenedecanamide (PXD-12), polybiscyclohexylmethanedecanamide (PCM-12), or a copolymer of some of these amides.

Furthermore, the fiber of the invention may be formed of a resin composition including an elastomeric resin as a main component, wherein "main component" refers to the component of the highest concentration. An elastomeric resin is a polymer that shows characteristics as an elastic body similar to those of vulcanized rubber at room temperature (20-30° C.) due to the soft segments in the molecule, and is susceptible to usual spinning technology for thermoplastics at high temperatures due to the hard segments in the molecule. Examples of elastomers include polystyrene elastomers, polyolefin elastomers, polyester elastomers, polyamide elastomers, and polyurethane elastomers.

Either single fiber including one uniform thermoplastic resin or conjugate fiber including two or more thermoplastic resins may be employed for the deodorant fiber of this invention. For conjugate fiber including two components to have satisfactory thermal bonding characteristics, it is recommended that the first component resin has a melting point lower than that of the second component resin, and is exposed on the fiber surface. The usual processing method for single fiber such as coating with a binder or physical entanglement by needle punching or spunlacing may cover the deodorant with the binder or remove the agent with the needle or water jet. The use of conjugate fiber minimizes this problem because thermal processing can be carried out.

The conjugate fiber used in the invention may be arranged as a conjugate formation of sheath-core, side-by-side, eccentric sheath-core, layered, radial or sea-island structures. The combination of the first/second components of the fiber may be polyolefin/polyolefin, polyolefin/polyester, polyester/polyester, polyamide/polyester, or polyolefin/polyamide. Examples of the polyolefin/polyolefin combinations include: high-density polyethylene/polypropylene, linear low-density polyethylene/polypropylene, low-density polyethylene/polypropylene, binary or ternary copolymer of propylene with other α-olefin(s)/polypropylene, linear low-density polyethylene/high-density polyethylene, and low-density polyethylene/high-density polyethylene. Examples of polyolefin/polyester combinations include: polypropylene/polyethylene terephthalate, high-density polyethylene/polyethylene terephthalate, linear low-density polyethylene/polyethylene terephthalate, and low-density polyethylene/polyethylene terephthalate. An example of the polyester/polyester combinations is copolyester/polyethylene terephthalate.

The cross section of the deodorant fiber of the invention may be circular or non-circular; examples of the non-circular shape of the cross section include star-shape, ellipse, triangle, square, pentagon, leaf-shape, dumbbell, T-shape and U-shape. The fiber with any of these cross section shapes may also be hollow. Additives including antioxidants, light stabilizers, UV absorbers, neutralizers, nucleation agents, epoxy stabilizers, smoothers, antibacterial agents, flame retardants, antistatic agents, pigments and plasticizers, may be used in the invention as long as the desirable properties of the invention are maintained.

The complex oxide used in this invention not only endows the fiber with deodorizing capacity but also improves the heat resistance of the component A of the fiber treating agent. The composition used in the component A can have a relatively low molecular weight or boiling point, which may lead, in the manufacturing process of nonwovens, particularly in the steps involving thermal bonding, to partial loss of the composition due to evaporation or penetration of the molten composition into the fiber, thus somewhat reducing the deodorizing activity of the product. Partially activated metal in said complex oxide mitigates such effects by combination with the component A or by enhancing the heat resistance of the oxide crystals or their secondary aggregates. Therefore, the deodorizing activity is best obtained by using the component A and a complex oxide together in the same fibers. Simple admixture of fiber containing a complex oxide alone with one containing the component A alone would not show satisfactory deodorizing performance.

Deposition of the complex oxide onto the fiber is best performed by kneading of the same into the fiber in a form of powder or master batch. Deposition of a slurry mixture of the oxide with the fiber treating agent is also acceptable. Deposition of the fiber treating agent may be performed using various techniques, such as contact with the oiling rollers in the spinning and/or stretching step, dipping, or spraying. The agent may also be deposited onto the web or shaped body of the fiber, e.g. by contact, dipping or spraying in the forming process of nonwovens. While the components A to C and the complex oxide may be deposited simultaneously in a slurry form, a preferable process includes first depositing the component A in the spinning, stretching or nonwoven forming step, followed by applying the surfactant containing the component B and/or component C. This technique is effective in suppressing electrostatic charge during the fiber opening process and minimizing loss of the component A because the component A is protected by the component B and/or C layered thereupon. The provision of the component A and the component B and/or C in separate steps still is considered to provide a surfactant composition or an agent that contains a surfactant composition for purposes of the present invention, i.e. the surfactant composition is viewed relative to the components provided for the fiber, regardless of the order in which they are provided. The term coated or coating indicates the presence of the components A and B and/or C on the exterior of the fiber, and does not preclude the presence of an intervening layer or a further coating layer. The coating agent preferably but not necessarily is provided uniformly.

An example of the deposition process includes depositing the component A, e.g. using a touching roller, during spinning, which may be performed by the known dry, wet, gel or melt spinning technique, and subsequently depositing the component B and/or C onto the layer of the component A.

Another example of the deposition process includes depositing the component A using a touching roller or a gravure roller on the nonwoven fabric manufactured by the known web/water-jet, short fiber/air-laying/thermal bonding, melt blowing/thermal bonding or spunbonding/thermal bonding process, and subsequently depositing the component B and/or C onto the layer of the component A. It should be noted that these examples do not limit the scope of the invention.

The deodorant fiber according to the invention may be formed into a fibrous article, for example, mesh, web, knit or nonwoven fabric, the last mentioned being particularly preferable. Nonwoven fabric may be manufactured by any of known processes, such as thermal bonding (through-air, point bonding), air-laying, needle punching or water jet processes. Web may be manufactured by carding of short fiber or melt blowing, or spunbonding can be performed for nonwoven fabric in the abovementioned processes. Mixed fibers, fabricated by fiber blending, mix spinning, mix weaving, twisting or knitting, also may be formed into fabric by the abovementioned processes. The fibrous articles manufactured according to the invention may be used either singly, or as laminate or other combined forms with different nonwovens, knits, mesh or film.

The deodorant fiber, or a fibrous articles obtained therefrom, according to the invention is applicable to various fiber products, including absorptive products such as diapers, sanitary napkins and urine collection pads; hospital/surgical gowns; interior finishing materials such as wall sheet and flooring; home products such as cover cloth and garbage cover sheet; hygiene products such as disposable toilets and toilet bowl covers; products for pets such as sheet, diaper and towel; general medical products; bedclothes; filters; and nursing care products.

The fiber according to the invention or nonwoven fabric made thereof has not only deodorizing activity but also protective effects for the skin against dermatitis such as diaper rash, and is therefore particularly suitable for diapers and other absorptive materials. For example, contact of bacteria or enzymes on the skin with urine generates ammonia to increase the pH value of the skin, which enhances the activity of proteinases or lipases, giving rise to diaper rash. The carboxyl and carbonyl groups in the component A, however, react with ammonia, thus maintaining the skin pH and preventing diaper rash. The buffering action of the carboxyl and carbonyl groups also contributes to pH control.

Furthermore, the complex oxide of at least two metals selected from a group comprising bivalent and trivalent metals may have a desiccant effect for the surface of the fiber. This effect endows the product according to this invention with astringent, anti-inflammatory and anti-allergic activity. In addition, the dry state controls proliferation of mites by affecting the water balance in their body and thus disrupts their reproduction.

EXAMPLES

The invention is now described further in detail by means of several illustrative but not limiting examples. Evaluation of the characteristics of the product in each example was performed as follows:

(Melt Flow Rate)

Melt flow rate was determined according to JIS K 7210.

MI was measured under the "Condition No. 4" in "Table 1", and MFR according to the "Condition No. 14" ("words in quotation marks" are corresponding to the same words in JIS K 7210).

(Antistatic Characteristics)

Web was manufactured out of 50 g of the fiber using a roller carding testing machine at a rate of 7 m/min at a temperature of 20° C. and a humidity of 45%. The antistatic performance on passage through the carding roller was evaluated in terms of the electrostatic voltage produced and the appearance of the web, and presented as the following scores:

****: Less than 100 V; negligible charge, good appearance of the web.

***: 100 V-1 kV; limited charge; good appearance of the web.

**: 1-3 kV; some disturbance in appearance due to charge observed.

*: 3 kV or more; extensive disturbance in appearance, heavy windup on the fly comb prohibiting processing.

(Adherence to the Fiber)

Web was manufactured out of 50 g of the fiber using a roller carding testing machine at a rate of 7 m/min at a temperature of 20° C. and a humidity of 45%. After stopping the machine, loss of the agent was evaluated as follows:

***: No dust of separated fiber treating agent observed.

**: Some dust observed.

*: A large amount of dust observed.

(Amount of Fiber Treating Agent Deposited)

The relative weight of the fiber treating agent deposited on the fiber was determined by measuring the weight difference of the fiber before and after dipping in an ethanol-water (50/50) mixture for 10 minutes at 60° C., dehydrating, dipping again in the same mixture for 10 minutes at 60° C., and drying, and using the formula:

$$\text{Amount deposited (weight \%)} = [(W_1 - W_2)/W_2] * 100$$

where $W_1$ is the weight of the dry fiber before dipping, in g, and $W_2$ the weight of the dry fiber after dipping, in g. $W_1$ was 3 g in actual tests.

(Deodorizing Activity)

The deodorizing performance against ammonia, acetic acid and hydrogen sulfide of the fibers manufactured in the Examples and Comparative examples described below was measured as follows. Three grams of the nonwoven sample was placed in a five-liter Tedlar bag and sealed. Air containing a specified amount of malodorous substance was then injected into the bag from a syringe to a total gas volume of 3 l. After a lapse of specified time, the gas in the bag was tested using a gas detector tube (Gastec Corporation, model 3La or 3L for ammonia, model 81 for acetic acid, model 4LL or 4LT for hydrogen sulfide). The elimination rate of the malodorous component was calculated by the formula:

$$\text{Elimination rate (\%)} = [(C_0 - C)/C_0] * 100$$

where $C_0$ is the initial concentration of the malodorous gas, and $C$ the concentration after a lapse of specified time.

Example 1

(Preparation of Deodorant Fiber)

The complex oxide used in this Example was one that was obtained according to the Example 1 of JP11-209258. Analysis showed its composition as $Zn_{0.75}Al_{0.25}O$. A mixture of 4 weight % of the oxide and 96 weight % of crystalline high-density polyethylene (ethylene homopolymer, melting point 131° C., MI 16 g/10 min, denoted as PE hereinafter) was used for the sheath of the fiber, whereas crystalline polypropylene (propylene homopolymer, melting point 163° C., MFR 16 g/10 min., denoted as PP) was used for the core. The proportion of PE and PP was 50/50 in terms of volume. These starting materials were spun through a sheath-core type nozzle at 250° C. producing yarn of a fineness of 8.5 dtex before stretching. The yarn was subsequently stretched in a roller machine at 90° C. with a stretching ratio of 4.5 (maximum rupture ratio 5.3). The fiber treating agent #1 (a mixture of the components A, B and C) (see Table 2 for composition) was deposited on the fiber during the stretching process. The stretched fiber was cut into staple. The sheath-core conjugate staple fiber had a net fineness of 2.2 dtex and a length of 51 mm. The resin compositions in the core and sheath are shown in Table 1 along with the amount of the complex oxide and treating agent. Note that the amount of the oxide is represented as the weight ratio with respect to the fiber.

(Manufacture of Nonwoven Fabric)

The fiber was formed into web by a roller carding machine, and heat treated by a suction band dryer (133° C.) to obtain through-air (TA) nonwoven fabric with a basis weight of 50 g/m$^2$. The deodorizing performance of the cloth obtained is shown in Table 1. This nonwoven fabric shows a very good performance against ammonia, acetic acid and hydrogen sulfide.

Example 2

(Preparation of Deodorant Fiber)

A mixture of 5 weight % of the same complex oxide as used in Example 1 and 95 weight % of crystalline polypropylene (propylene homopolymer. melting point 163° C., MFR 16 g/10 min.) was spun. The fiber treating agent #2 (a mixture of the components A and B) was deposited on the fiber during the subsequent stretching process, and the stretched fiber was cut into staple with a net fineness of 3.3 dtex and a length of 64 mm.

(Manufacture of Nonwoven Fabric)

The fiber was formed into web by a roller carding machine, and processed in a needle punching (NP) machine to obtain nonwoven fabric with a basis weight of about 100 g/m$^2$. The deodorizing performance of the cloth obtained is shown in Table 1.

Example 3

(Preparation of Deodorant Fiber)

A mixture of 6 weight % of the same complex oxide as used in Example 1 and 94 weight % of ethylene-butene-propylene copolymer (4 wt % ethylene, 5 wt % butene, 91 wt % propylene; melting point 131° C., MFR 16 g/10 min, denoted as co-PP) was used for the sheath of the fiber, whereas crystalline polypropylene (propylene homopolymer. melting point 163° C., MFR 16 g/10 cm, denoted as PP) was used for the core. These starting materials were spun through a sheath-core nozzle at 280° C., and subsequently processed as in Example 1 into sheath-core conjugate staple fiber with a net fineness of 2.2 dtex and a length of 38 mm.

(Manufacture of Nonwoven Fabric)

The fiber was formed into web by a roller carding machine, and heat treated by an embossing machine (roller temperature 126° C., linear pressure 20 kg/cm (corresponding to $1.96 \times 10^2$ N/cm), embossing area ratio 25%) to obtain point-bonded (PB) nonwoven fabric with a basis weight of about 50 g/m$^2$. The deodorizing performance of the cloth obtained is shown in Table 1.

Example 4

(Preparation of Deodorant Fiber)

A mixture of 1 weight % of the same complex oxide as used in Example 1 and 99 weight % of crystalline high-density polyethylene (ethylene homopolymer, melting point 131° C., MI 16 g/10 min) was used for the sheath of the fiber, whereas polyethylene terephthalate (limit viscosity η=0.635, denoted as PET) was used for the core. The proportion of the resins was 50/50 in terms of volume. These starting materials were spun through a sheath-core nozzle at 280° C. The fiber treating agent #3 (a mixture of the components A and C) was deposited on the fiber during the subsequent stretching process, and the stretched fiber was cut into staple with a net fineness of 2.2 dtex and a length of 51 mm.

(Manufacture of Nonwoven Fabric)

The staple was formed into nonwoven fabric according to the same manner in Example 1, and tested for the deodorizing performance as in Example 1.

Example 5

(Preparation of Deodorant Fiber)

A mixture of 2 weight % of the same complex oxide as used in Example 1 and 98 weight % of crystalline high-density polyethylene (ethylene homopolymer, melting point 131° C., MI 16 g/10 min) was used as the first component, and crystalline polypropylene (propylene homopolymer, melting point 163° C., MFR 16 g/10 min) as the second component. The proportion of the resins was 50/50 in terms of volume. These starting materials were spun through a side-by-side spinning nozzle at 250° C. The fiber treating agent #1 was deposited on the fiber during the subsequent stretching process, and the stretched side-by-side union fiber was cut into staple with a net fineness of 2.2 dtex and a length of 38 mm.

(Manufacture of Nonwoven Fabric)

The staple was formed into nonwoven fabric according to the same manner in Example 1, and tested for the deodorizing performance as in Example 1.

Example 6

The same complex oxide as used in Example 1 was dispersed in water to prepare a slurry containing 15 wt % solid, to which the fiber treating agent #2 was added. A sheath-core conjugate fiber was prepared using crystalline high-density polyethylene (ethylene homopolymer, melting point 131° C., MI 16 g/10 min) as the sheath and crystallline polypropylene (propylene homopolymer, melting point 163° C., MFR 16 g/0 min) as the core. The slurry including the fiber treating agent #2 prepared above was deposited on the fiber during the stretching process. The fiber was cut into staple, which was processed into nonwoven fabric. The staple had a net fineness of 2.2 dtex and a length of 45 mm. The amount deposited of the oxide and the total amount deposited of the oxide plus fiber treating agent are shown in Table I.

(Manufacture of Nonwoven Fabric)

The staple was formed into nonwoven fabric according to the same manner in Example 1, and tested for the deodorizing performance as in Example 1.

Comparative Example 1

Nonwoven fabric was prepared in the same processes as in Example 1, except for the use of the fiber treating agent #4 (a mixture of the components B and C). The deodorizing performance of the cloth obtained is shown in Table 1. It was relatively effective against acetic acid and hydrogen sulfide, but rather poor against ammonia.

Comparative Example 2

Nonwoven fabric was prepared in the same processes as in Example 1, except that the sheath and core consisted of crystalline high-density polyethylene (ethylene homopolymer, melting point 131° C., MI 16 g/10 min) and crystalline polypropylene (propylene homopolymer, melting point 163° C., MFR 16 g/10 min), respectively. The deodorizing performance of the cloth obtained is shown in Table 1. It was effective against ammonia only. Performance against acetic acid and hydrogen sulfide was poor.

Comparative Example 3

Nonwoven fabric was prepared in the same processes as in Example 1, except for the use of the fiber treating agent #5 containing the component A only. The fiber generated dust in the carding machine due to separation of the fiber treating agent. The web had a disordered appearance, and was difficult to process because of windup around the fly comb.

Comparative Example 4

The union fiber obtained in Comparative example 1 (complex oxide only was added) and that obtained in Comparative example 2 (components A, B and C only were added) were blended at a weight ratio of 50/50, and processed in the same manner as in Example 1 to prepare nonwoven fabric. Deodorizing tests were performed using a sample weight of 6 g so that the weights of the components were comparable with those in samples from other Examples. The deodorizing performance of the fabric obtained is shown in Table 1. The effect against ammonia was slightly lower than the fabric obtained in Example 1 containing both complex oxide and the components A, B and C.

Comparative Example 5

Nonwoven fabric was prepared in the same processes as in Example 1, except that the sheath and core consisted of crystalline high-density polyethylene (ethylene homopolymer, melting point 131° C., MI 16 g/10 min) and crystalline polypropylene (propylene homopolymer, melting point 163° C., MFR 16 g/10 min), respectively, and that a fiber treating agent #4 (a mixture of the components B and C) was deposited onto the fiber. The deodorizing performance of the fabric obtained is shown in Table 1. It showed rather poor activity against ammonia, acetic acid and hydrogen sulfide.

Example 7

Two garbage cover sheets were manufactured using the nonwoven fabric obtained in Example 1 and Comparative example 5, respectively, and field tests were performed for their deodorant performance. The cover sheet based on the fiber from Example 1 showed performance superior to that of one from Comparative example 5 in that it eliminated the odor of garbage almost completely.

Example 8

Two diapers were manufactured using the nonwoven fabric obtained in Example 3 and Comparative example 5, respectively, as the backing sheet, and tested for effectiveness against urine odor by impregnating with 100 ml each of human urine, wrapping in adhesive tape, and storing each in a sealed bag for a day. Example 3 shows that urine odor was eliminated far more effectively by the diaper based on Example 1 than that based on Comparative example 5.

TABLE 1

| | | | Example 1 | Example 2 | Example 3 | Example 4 | Example 5 | Example 6 |
|---|---|---|---|---|---|---|---|---|
| Composition of the invention | Complex oxide | Content | 2 | 5 | 3 | 0.5 | 1 | 0.5 |
| | | Method of addition | Kneading | Kneading | Kneading | Kneading | Kneading | Surface deposition |
| | Fiber treating agent | Composition | #1 | #2 | #1 | #3 | #1 | #2 |
| | | Amount deposited | 1.1 | 1 | 1.1 | 1.1 | 0.9 | 1.5 |
| Fiber | Resin | Cross section | Sheath-core | Mono component | Sheath-core | Sheath-core | Side-by-side | Sheath-core |
| | | Core material | PP | PP | PP | PET | PP | PP |
| | | Sheath material | PE | — | co-PP | PE | PE | PE |
| | Passage through carding machine | Antistatic performance | **** | *** | **** | *** | **** | **** |
| | | Adherence to the fiber | ** | ** | ** | ** | ** | ** |
| | | Processing method | TA | NP | PB | TA | TA | TA |
| Deodorant performance test | Ammonia | 0 min | 60 ppm | 60 ppm | 60 ppm | 60 ppm | 60 ppm | 60 ppm |
| | | 15 min | 15 ppm | 10 ppm | 1 ppm | 20 ppm | 12 ppm | 8 ppm |
| | | 2 hr | 4 ppm | 2 ppm | 0 ppm | 10 ppm | 1 ppm | 2 ppm |
| | | 24 hr | 0 ppm | 0 ppm | 0 ppm | 3 ppm | 1 ppm | 0 ppm |
| | | Removal ratio (%) | 100 | 100 | 100 | 95 | 99 | 100 |
| | Acetic acid | 0 min | 50 ppm | 50 ppm | 50 ppm | 50 ppm | 50 ppm | 50 ppm |
| | | 15 min | 18 ppm | 10 ppm | 11 ppm | 25 ppm | 20 ppm | 8 ppm |
| | | 2 hr | 5 ppm | 2 ppm | 2 ppm | 15 ppm | 11 ppm | 2 ppm |
| | | 24 hr | 3 ppm | 0 ppm | 0 ppm | 5 ppm | 4 ppm | 0 ppm |
| | | Removal ratio (%) | 94 | 100 | 100 | 90 | 92 | 100 |
| | Hydrogen sulfide | 0 min | 15 ppm | 15 ppm | 15 ppm | 15 ppm | 15 ppm | 15 ppm |
| | | 15 min | 0.1 ppm | 0 ppm | 0 ppm | 5 ppm | 1 ppm | 0 ppm |

TABLE 1-continued

|  |  |  | 2 hr | 0 ppm | 0 ppm | 0 ppm | 1 ppm | 0 ppm | 0 ppm |
|---|---|---|---|---|---|---|---|---|---|
|  |  |  | 24 hr | 0 ppm | 0 ppm | 0 ppm | 0 ppm | 0 ppm | 0 ppm |
|  |  |  | Removal ratio (%) | 100 | 100 | 100 | 100 | 100 | 100 |

|  |  |  |  | Comparative example 1 | Comparative example 2 | Comparative example 3 | Comparative example 4 | Comparative example 5 |
|---|---|---|---|---|---|---|---|---|
| Composition of the invention | Complex oxide | Content | 2 | — | 2 | 2 | — |
|  |  | Method of addition | Kneading | — | Kneading | Kneading | — |
|  | Fiber treating agent | Composition | #4 | #1 | #5 | #1 | #4 |
|  |  | Amount deposited | 0.5 | 1.1 | 0.6 | 1.1 | 0.5 |
| Fiber | Resin | Cross section | Sheath-core | Sheath-core | Sheath-core | Sheath-core | Sheath-core |
|  |  | Core material | PP | PP | PP | PP | PP |
|  |  | Sheath material | PE | PE | PE | PE | PE |
|  | Passage through carding machine | Antistatic performance | **** | **** | * | **** | **** |
|  |  | Adherence to the fiber | ** | ** | * | ** | ** |
|  | Processing method |  | TA | TA | TA | TA | TA |
| Deodorant performance test | Ammonia | 0 min | 60 ppm | 60 ppm | — | 60 ppm | 60 ppm |
|  |  | 15 min | 50 ppm | 13 ppm | — | 30 ppm | 60 ppm |
|  |  | 2 hr | 45 ppm | 3 ppm | — | 15 ppm | 55 ppm |
|  |  | 24 hr | 33 ppm | 0 ppm | — | 8 ppm | 45 ppm |
|  |  | Removal ratio (%) | 45 | 100 | — | 86 | 25 |
|  | Acetic acid | 0 min | 50 ppm | 50 ppm | — | 50 ppm | 50 ppm |
|  |  | 15 min | 17 ppm | 40 ppm | — | 20 ppm | 45 ppm |
|  |  | 2 hr | 7 ppm | 30 ppm | — | 8 ppm | 41 ppm |
|  |  | 24 hr | 2 ppm | 18 ppm | — | 3 ppm | 35 ppm |
|  |  | Removal ratio (%) | 95 | 64 | — | 94 | 30 |
|  | Hydrogen sulfide | 0 min | 15 ppm | 15 ppm | — | — | 15 ppm |
|  |  | 15 min | 0 ppm | 15 ppm | — | — | 15 ppm |
|  |  | 2 hr | 0 ppm | 14 ppm | — | — | 14 ppm |
|  |  | 24 hr | 0 ppm | 13 ppm | — | — | 13 ppm |
|  |  | Removal ratio (%) | 100 | 13 | — | — | 13 |

TABLE 2

|  |  |  | Fiber treating agent #1 | Fiber treating agent #2 | Fiber treating agent #3 | Fiber treating agent #4 | Fiber treating agent #5 |
|---|---|---|---|---|---|---|---|
| Composition of the invention | (A) | N,N-Dimethyl-N-dodecanoylaminopropylbetaine | 32 |  | 30 |  | 60 |
|  |  | 2-Undecyl-N-carboxymethyl-N-imidazolium betaine |  | 30 |  |  |  |
|  |  | Glyoxylic acid | 17 |  | 12 |  | 24 |
|  |  | Pyruvic acid | 1 |  | 1 |  | 2 |
|  |  | Glyoxal |  | 15 |  |  |  |
|  |  | Ricinolic acid |  | 5 |  |  | 10 |
|  |  | Methyl vinyl ether-maleic anhydride copolymer |  |  | 7 |  |  |
|  | (B) | Sorbitan monoleate |  | 50 |  |  |  |
|  |  | Sorbitan monopalmitate | 20 |  |  | 40 |  |
|  |  | Stearic acid EO(5) |  |  |  |  |  |
|  |  | (C12) Alcohol EO(10) |  |  |  |  |  |
|  | (C) | (C12) Alkyl phosphate potassium salt | 15 |  |  | 30 |  |
|  |  | (C18) Alkyl phosphate potassium salt | 15 |  | 30 | 30 |  |
|  |  | (C22) Alkyl phosphate potassium salt |  |  | 20 |  |  |

The present invention provides deodorant fiber including a thermoplastic resin containing a complex oxide of at least two metals selected from a group consisting of bivalent and trivalent metals onto which fiber treating agent component A and component B and/or component C are deposited. The deodorizing agent is also antibacterial, antistatic and heat-resistant, and is not easily separated from fiber surface. The fiber is furthermore antistatic and heat-resistant. A particular advantage of the fiber is the effectiveness against all of the three principal classes of malodorous substances, i.e. bases such as ammonia and amines, acids such as acetic acid, and sulfur-containing compounds such as hydrogen sulfides. The fiber presents also a high absorption rate.

The fiber according to invention further provides fibrous articles and fiber products with excellent deodorizing, antibacterial, antifungal, acaricidic and anti-allergic performance. Potential applications include absorptive products such as diapers, sanitary napkins and urine collection pads;

hospital/surgical gowns; interior finishing materials such as wall sheet and flooring; home products such as cover cloth and garbage cover sheet; hygiene products such as disposable toilets and toilet bowl covers; products for pets such as sheet, diaper and towel; general medical products; bedclothes; filters; and nursing care products.

While a detailed description of the present invention has been provided, the present invention is not limited thereto, and modifications will be apparent. The invention is defined by the claims that follow.

What is claimed is:

1. A deodorant fiber comprising a thermoplastic resin containing 0.1 to 10 weight %, with respect to the weight of said fiber, of a complex oxide kneaded into the fiber, and a surface of the fiber being coated with 0.3 to 5 weight %, with respect to the weight of said fiber, of coating comprising a surfactant composition comprising 20-80 weight % of a component A and 80-20 weight % of at least one component selected from the group consisting of a component B and a component C,
  the complex oxide being represented by either the following formula (1):

$$M^{2+}_{(1-x1)}M^{3+}_{(x1-\delta)}O \qquad (1),$$

wherein $M^{2+}$ is zinc or a zinc-containing divalent metal; $M^{3+}$ is a trivalent metal selected from a group consisting of Al, Fe and Ce; x1 is a number in a range $0<x1\leq 0.5$; and $\delta$ is cationic lattice defect,
  or the following formula (2):

$$(M_1^{2+})_{1-x2}(M_2^{2+})_{x2}O \qquad (2),$$

wherein $M_1$ is at least one member selected from the group consisting of Mg and Ca; $M_2$ is at least one member selected from the group consisting of Cu and Zn; and x2 is a number in a range $0.0001\leq x_2\leq 0.5$,
  the component A being at least one compound selected from a group consisting of betaine amphoteric compounds, carbonyl compounds and vinyl ether-maleic anhydride copolymers, the carbonyl compounds being at least one selected from the group consisting of monovalent aldehydes, bivalent aldehydes, aromatic aldehydes, aldehydic alcohols, aldehydic carboxylic acids, ketones, ketoaldehydes, ketoalcohols, and ketocarboxylic acids,
  the component B being a nonionic surfactant including at least one substance selected from a group consisting of nonionic surfactants based on alkylene oxide adducts and nonionic surfactants based on polyvalent alcohols, and
  the component C is an anionic surfactant including at least one substance selected from a group consisting of carbonates, sulfonates, sulfate ester salts and phosphate ester salts,
  the carbonates being at least one selected from the group consisting of soaps of potassium oleate and soaps of sodium laurate,
  the sulfonates being at least one selected from the group consisting of alkylsulfonates and alkylbenzenesulfonates,
  the sulfate ester salts being at least one selected from the group consisting of alkyl sulfate ester salts or alkyl (polyoxyalkinene) sulfate ester salts,
  the phosphate ester salts are phosphate ester salts of higher alcohols having 6 to 24 carbon atoms.

2. The deodorant fiber according to claim 1, being a conjugate fiber comprising at least two thermoplastic resins, 0.1-10 weight %, with respect to the weight of said fiber, of said complex oxide having been kneaded into at least one of said thermoplastic resins, the surface of said conjugate fiber being coated with 0.3 to 5 weight %, with respect to the weight of said fiber, of an coating comprising a surfactant composition comprising 20-80 weight % of the component A and 80-20 weight % of the at least one component selected from the group consisting of the component B and the component C.

3. The deodorant fiber according to claim 2, wherein said fiber is a sheath-core conjugate fiber, said complex oxide being kneaded into the sheath component of said fiber.

4. The deodorant fiber according to claim 1, wherein 0.1 to 4 weight %, with respect to the weight of said fiber, of said component A is deposited onto said fiber.

5. A fibrous article comprising the deodorant fiber according to claim 1.

6. A fiber product comprising the deodorant fiber according to claim 1.

7. A fiber product comprising the deodorant fiber according to claim 5.

8. The deodorant fiber according to claim 1, wherein
  the monovalent aldehydes, when present, being at least one selected from the group consisting of crotonaldehyde, allyl aldehyde, cinnamic aldehyde, octyl aldehyde, nonyl aldehyde and citronellal;
  the bivalent aldehyde, when present, is a glyoxal;
  the aromatic aldehyde, when present, is a benzaldehyde;
  the aldehydic alcohol, when present, is a glycol aldehyde;
  the aldehydic carboxylic acids, when present, being at least one selected from the group consisting of glyoxylic acid, lactaldehyde, and glucuronic acid;
  the ketones, when present, being at least one selected from the group consisting of acetone, methyl ethyl ketone, dibutyl ketone, ionones, acetylacetone, and benzophenone;
  the ketoaldehyde, when present, is a methylglyoxalic acid;
  the ketoalcohols, when present, being at least one selected from the group consisting of acetol and dimethylketol; and
  the ketocarboxylic acids, when present, being at least one selected from the group consisting of pyruvic acid, benzoylformic acid, phenylpyruvic acid, acetoacetic acid, propionylacetic acid, benzoylacetic acid, levulinic acid, and β-benzoylpropionic acid.

9. The deodorant fiber according to claim 1, wherein the alkylsulfonates being at least one selected from the group consisting of sodium lauryl sulfonate and sodium cetylsulfonate; and the alkylbenzenesulfonates is lauryl benzenesulfonate.

10. The deodorant fiber according to claim 1, wherein the alkyl sulfate ester salt is sodium stearyl sulfate; and the alkyl (polyoxyalkinene) sulfate ester salts is a sodium salt of sulfuric acid ester of adducts of lauryl alcohol with oxyalkylenes.

11. The deodorant fiber according to claim 1, wherein the phosphate ester salts of higher alcohols being at least one selected from the group consisting of stearyl alcohol and adducts thereof with polyoxyalkylenes.

12. The deodorant fiber according to claim 1, wherein x1 is a number in a range $0.1\leq x1\leq 0.5$.

* * * * *